United States Patent [19]

Ramachandran et al.

[11] Patent Number: 4,990,632

[45] Date of Patent: Feb. 5, 1991

[54] PROCESS FOR THE PRODUCTION OF OXIDES

[75] Inventors: Ramakrishnan Ramachandran, Allendale; Donald L. Maclean, Annandale; Donald P. Satchell, Jr., Summit, all of N.J.

[73] Assignee: The BOC Group, Inc., Murray Hill, N.J.

[21] Appl. No.: 376,338

[22] Filed: Jul. 6, 1989

Related U.S. Application Data

[63] Continuation-in-part of Ser. No. 215,858, Jul. 6, 1988, Pat. No. 4,849,538, which is a continuation-in-part of Ser. No. 172,112, Mar. 23, 1988, abandoned.

[51] Int. Cl.$^5$ .................. C07D 301/04; C07D 301/08; C07D 301/10
[52] U.S. Cl. .................................... 549/523; 549/534; 549/535; 549/536; 568/411; 568/475; 585/654; 585/659
[58] Field of Search ................ 549/523, 534, 535, 536

[56] References Cited

U.S. PATENT DOCUMENTS

| | | | |
|---|---|---|---|
| 3,176,444 | 4/1965 | Kiyonaga | 55/26 |
| 4,498,910 | 2/1985 | Benkmann | 55/18 |
| 4,609,502 | 9/1986 | Khoobtar et al. | 558/319 |
| 4,754,049 | 6/1988 | Khoobtar et al. | 558/320 |
| 4,849,538 | 7/1989 | Ramachandran et al. | 558/319 |
| 4,868,330 | 9/1989 | Ramachandran et al. | 558/319 X |
| 4,870,201 | 9/1989 | Ramachandran et al. | 558/319 |

OTHER PUBLICATIONS

Solomons, "Organic Chemistry", p. 212, 2nd ed., (1978), John Wiley & Sons.

*Primary Examiner*—Joseph Paul Brust
*Attorney, Agent, or Firm*—Carol A. Nemetz; Robert I. Pearlman

[57] ABSTRACT

An improved process is provided for the production of oxides from hydrocarbons by reaction with oxygen, air or a gas enriched in oxygen relative to air, preferably the latter, in the presence of an oxidation catalyst. An alkane, e.g. propane, is converted to an alkene in a dehydrogenator. The product stream is introduced into an oxidation reactor. The product formed therein is recovered in a quench tower. The gas phase from the quench tower is treated in a PSA unit to form a gaseous stream containing the unreacted alkane, alkene, a minor amount of oxygen, i.e. less than about 2 percent by volume, and nitrogen if present in the feed to the oxidation reactor. The gaseous stream, which may or may not contain hydrogen depending on the adsorbent on the PSA unit, is introduced into a selective oxidation unit to remove the remaining oxygen and then recycled to the dehydrogenator. Hydrogen may be introduced into or removed from the PSA effluent, depending on the function of the adsorbent therein, to obtain an optimum concentration for introduction into the dehydrogenator. A preferred PSA system for use in the subject process comprises two parallel PSA units containing differnt adsorbents such that the gaseous stream formed in one PSA unit contains all of the hydrogen from the gas phase of the quench tower. The feed to the PSA units is divided disaproportionately so that the combined PSA effluent recycle streams contain the optimum concentration of hydrogen for the dehydrogenator.

17 Claims, 4 Drawing Sheets

PROCESS FOR THE PRODUCTION OF OXIDES

RELATED APPLICATIONS

This application is a continuation in part of U.S. patent application Ser. No. 07/215,858, filed July 6, 1988, which is a continuation-in-part of U.S. patent application Ser. No. 07/172,112, filed Mar. 23, 1988, now abandoned.

The present invention is directed to a process for producing alkylene oxides from alkane and an oxygen-containing gas in the presence of an oxidation catalyst under conditions which achieve high efficiency and selectivity toward the desired product.

BACKGROUND OF THE INVENTION

The production alkylene of oxides by oxidation of an appropriate alkane in the presence of a suitable catalyst is well known.

Brian J. Ozero, *Handbook of Chemicals Production Processes*, edited by Robert Meeds, McGraw Hill Book Co. (1986) at Chapter 1.5, discusses cyclic processes using both oxygen and air as oxidant for the production of ethylene oxide (EO) from ethylene In these processes, the alkene is oxidized in a multitubular catalytic reactor in vapor phase. The reactor off gases are cooled and scrubbed with water in an absorber to recover ethylene oxide which is sent to the recovery section for further purification.

In the oxygen-based process described by Ozero, the scrubber off gases are divided into three parts which are: (i) recycled to the reactor, (ii) vented and (iii) sent to a separator for carbon dioxide removal and recycle of the remaining hydrocarbons. This process suffers from several disadvantages. For example, the oxygen-based ethylene oxide process requires a separate carbon dioxide removal unit and a purge to remove argon to prevent its accumulation.

In the air-based process described by Ozero, the scrubber off gases are sent to a second reactor, which is the purge reactor, where additional unreacted ethylene is reacted using a higher air to ethylene ratio, foregoing some EO selectivity. The reactor off gases are again passed through another water scrubber to recover EO produced. It is known that the volume of hydrocarbons purged, when utilizing air as a source of oxygen, requires that the purge scrubber off gases be incinerated to remove any remaining hydrocarbons in order to meet environmental regulations. In this air-based process, an additional purge oxidation reactor, a water scrubber, and an effluent incinerator are required, as well as a greater volume of catalyst. Also, both this and the oxygen-based process use the expensive ethylene as the raw material. The processes described by Ozero are limited to either pure oxygen or air.

Khoobiar et al., U.S. Pat. No. 4,609,502, discloses a cyclic process for producing acrylonitrile using propane as a starting material This process differs from the production of oxides by the presence of ammonia and the choice of catalyst. In the process disclosed by Khoobiar et al., the alkane is initially dehydrogenated catalytically in the presence of steam to form propylene. This is in contrast to most conventional dehydrogenation processes which avoid steam primarily due to the costs involved. After ammoxidation, the effluent is quenched to remove the desired product, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are byproducts of dehydrogenation, and unreacted propylene and propane, in addition to carbon oxides. A sufficient portion of this gas mixture is purged to remove the net production of carbon oxides and light hydrocarbons.

Optionally, this gas mixture is split and a portion sent to a separator which removes only carbon dioxide. A portion of the effluent from the separator is purged to remove light hydrocarbons. The nonpurged portion is mixed with the remainder of the oxidation reactor effluent, fresh propane, and steam, if necessary. This mixture is sent to the dehydrogenator where the propane is converted to propylene. Another option is to cool and liquify the $C_3$ hydrocarbons from the oxidation reactor, and then vaporize the hydrocarbons prior to recycle.

In the process disclosed by Khoobiar et al., there is no practical way to remove byproducts of propane dehydrogenation, such as methane, ethane, ethylene and the like, thereby preventing their accumulation in the system, other than by removing them in a purge stream. The removal of these gases in a purge stream will likewise result in a loss of the circulating propane and propylene, thus causing a significant decrease in the overall yield of propylene to acrylonitrile. While, as mentioned above, propane and propylene can be recovered from the stream prior to venting, this requires additional refrigeration apparatus to cool and liquify the propylene and propane. The separated $C_3$ hydrocarbons must be vaporized prior to recycle. These operations add to the capital and power requirements of the process.

Another disadvantage of the Khoobiar et al. process stems from the use of the selective oxidation reactor to treat the gaseous effluent exiting the quench tower. This quench effluent is at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three know methods to alleviate this problem. First, the amount of oxygen entering the oxidation reactor can be reduced by other means. Second, multiple reactors can be utilized with a cooling means between each pair of reactors. Third, a portion of the oxidation reactor can be passed through a cooling means and recycled to the feed to reduce the internal temperature of the reactor. None of these measures is attractive from the viewpoint of cost and efficiency.

The oxidation reactor in the Khoobiar et al. process is operated with oxidation catalysts such as noble metals (e.g., platinum). Olefins and carbon monoxide, which are generated in the dehydrogenation reactor, are known to deactivate these catalysts, as disclosed in Charles L. Thomas, Catalytic Processes and Proven Catalysts, Academic Press (1970) at 118–119. Accordingly, multiple oxidation reactors must be used (see Khoobiar et al. at column 4, lines 51–56) to allow for frequent regeneration of the catalyst which represents yet another addition to production costs. These consideration apply as well to the catalytic production of oxides from alkanes as contemplated herein.

It is therefore apparent that the industry is still searching for a cost effective process of converting alkanes into oxides. The process of the present invention is cost effective and substantially reduces or eliminates disadvantages of the aforementioned systems. Moreover, in comparison to conventional processes, the thermal requirements of the present invention process are markedly reduced.

SUMMARY OF THE INVENTION

A process is disclosed for the production of alkylene oxides comprising converting a gaseous alkane to the corresponding alkene in a dehydrogenator, reacting the alkene in an oxidation reactor with an oxygen-containing gas, preferably oxygen-enriched air, in the presence of an oxidation catalyst to form the desired oxide. The product stream is quenched with a liquid to form a liquid phase containing the desired product and a gas phase which is passed under pressure into a separator, such as a pressure swing adsorption unit, to remove carbon oxides, oxygen, nitrogen (if present), and lower hydrocarbons therefrom. The gaseous stream from the separator is passed into a selective oxidation unit where the remainder of the oxygen is removed. The effluent from the selective oxidation unit is recycled to the dehydrogenator with fresh propane feed.

DESCRIPTION OF THE PREFERRED EMBODIMENTS

The process of this invention is applicable to the synthesis of alkylene oxides. In each instance, an alkene, which has been formed by the dehydrogenation of the corresponding alkane, is reacted with an oxygen-containing gas comprising pure oxygen, air, or a gas enriched in oxygen relative to air, in the presence of a suitable catalyst. The term "suitable oxidation catalyst" indicates a catalyst that will catalyze the production of the desired product, e.g. ethylene oxide from ethylene or propylene oxide from propylene, under the conditions utilized in the reactor. That is, an oxirane ring or alkylene oxide will be formed. In the interest of brevity, the subject process will be described with reference to the production of propylene oxide from propane, but is in no way intended to be limited thereto.

Figure 1:
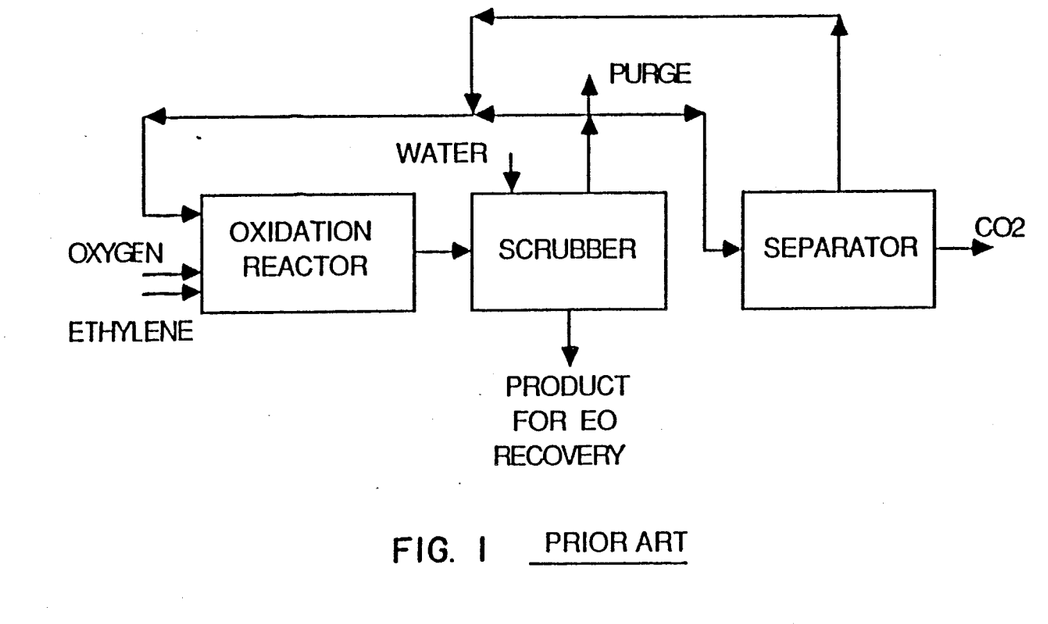
FIG. 1 illustrates in block diagram a conventional process for production of ethylene oxide from ethylene using oxygen.
Figure 2:
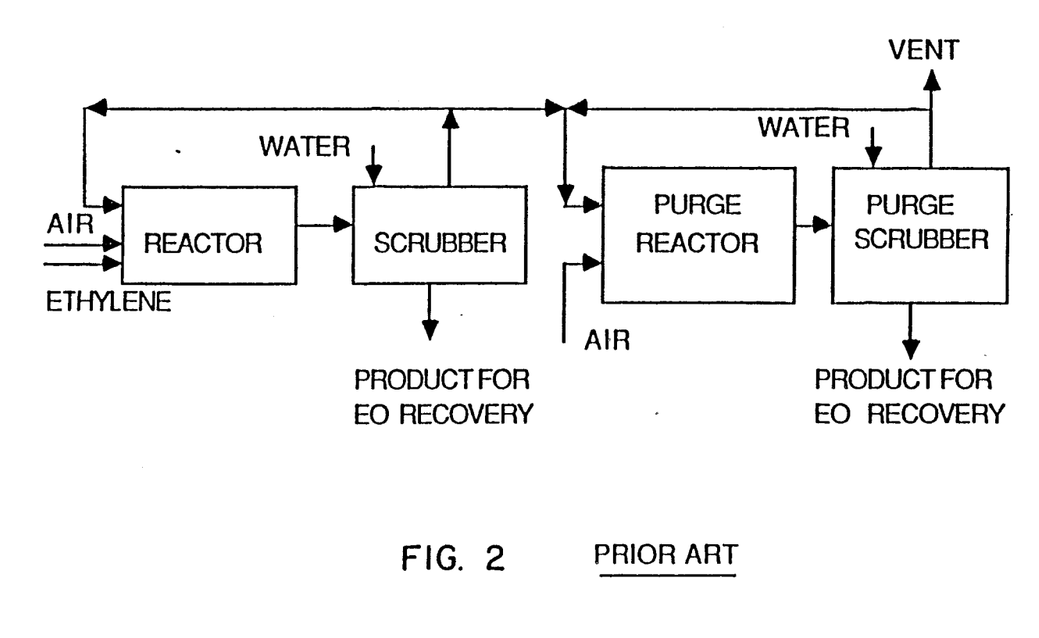
FIG. 2 illustrates in block diagram a conventional process for production of ethylene oxide from ethylene using air.

Turning to the drawings, a process currently utilized commercially to produce oxides such as ethylene oxide, is illustrated in FIGS. 1 and 2. In FIG. 1, ethylene and oxygen are fed into a conventional reactor containing a suitable oxidation catalyst; in FIG. 2, ethylene and air are similarly fed. The reactor may be of any conventional fixed or fluidized bed design. Such processes may employ a recycle step to increase the overall process efficiency. The oxygen concentration in the feed to the reactor is adjusted to maximize the selectivity to the desired product.

In the oxygen-based process, shown in FIG. 1, methane is added continuously to the reactor as a flame suppressor to compensate for the loss in the purge. The reactor off gases are sent to water scrubber to remove products for ethylene oxide recovery. The scrubber off gases are divided into three parts: a first part is recycled back to the reactor, a second part is vented, and a third part is sent to a $CO_2$ removal unit. After removing $CO_2$, the off gases of the third part are sent back to the reactor. The purge is essential to prevent any argon build up in the system. Since there is no other way to remove inerts from the system, one cannot use air or oxygen-enriched air as the oxidant feed since the large volume required to purge the nitrogen would cause excessive loss of product.

In the air-based process, shown in FIG. 2, ethylene and air are fed into the reactor. The reactor products are water scrubbed to remove the ethylene oxide produced. A part of the scrubber off gases are recycled back to the reactor while the remainder is sent to a second reactor. Additional air is added to this second reactor to achieve an air-to-ethylene feed ratio higher than the first reactor so that high ethylene conversion is obtained. The off gases of the second reactor are sent to a second water scrubber to remove and recover the additional ethylene oxide produced. The second scrubber off gases are split into two portions—one is recycled back to the second reactor while the other is purged, typically via incineration.

Figure 3:
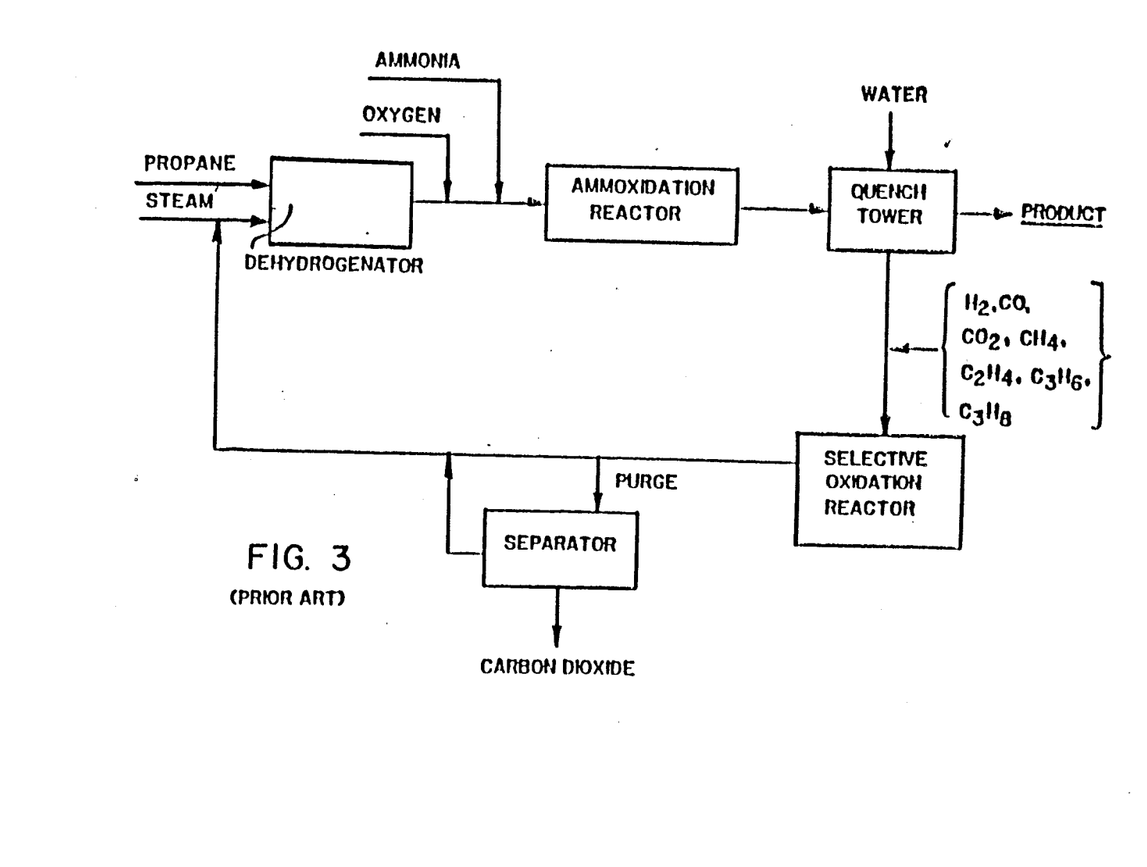
FIG. 3 illustrates in block diagram a conventional process, for production of acrylonitrile utilizing a recycle step.

FIG. 3 illustrates the cyclic process for producing acrylonitrile as disclosed in Khoobiar et al., U.S. Pat. No. 4,609,502. In this process, propane and steam are fed into a dehydrogenator to form propylene, which is then mixed with oxygen and ammonia and fed into an ammoxidation reactor. The product of the reactor is fed to an aqueous quench tower, and the products withdrawn in solution. The gaseous off gases from the quench tower, typically containing hydrogen, carbon monoxide, carbon dioxide, methane, ethylene, ethane, propane, propylene, and oxygen is fed to a selective oxidation reactor. It is generally essential for the efficient operation of such a reactor to heat the gas mixture prior to introduction therein.

A portion of the off gas from the selective oxidation reactor is passed to a separator to remove carbon dioxide by an undisclosed mechanism. A portion of the selective oxidation reactor effluent, which contains light hydrocarbons and hydrogen, is purged, treated to remove propane and propylene [not shown], and then discarded, thereby preventing buildup of byproducts in the system. The propane and propylene removed are combined [not shown] with the remainder of the selective oxidator effluent and the remainder of the separator effluent and recycled to the dehydrogenator. It is, of course, necessary for the selective oxidation reactor to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 4:
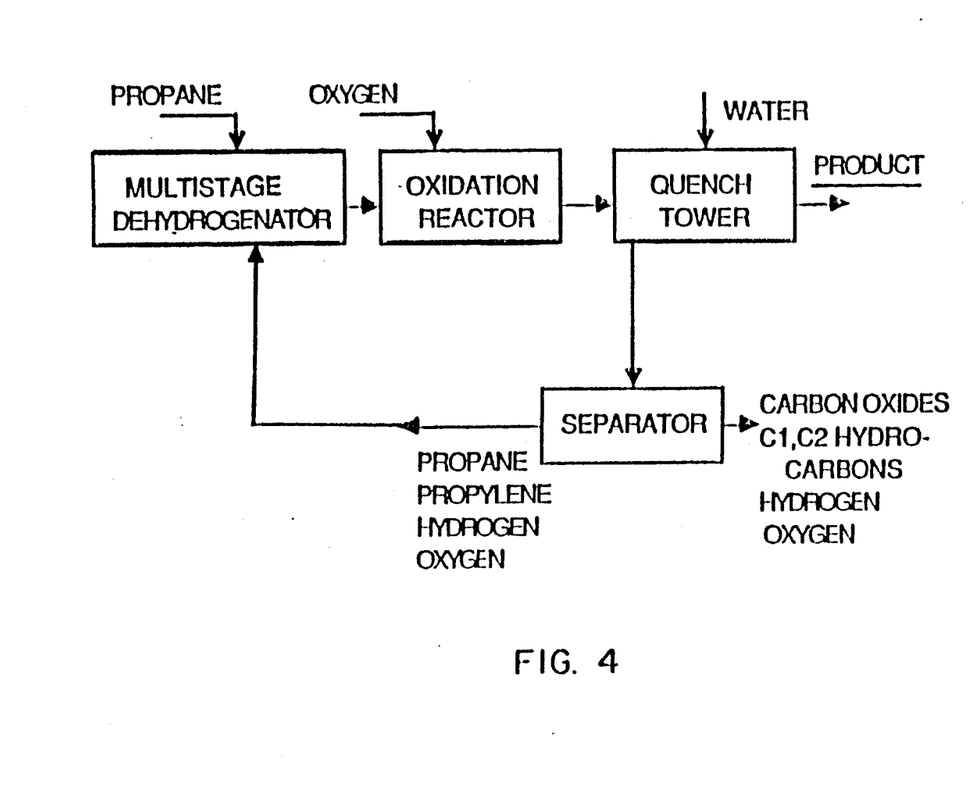
FIG. 4 illustrates in block diagram the process of the present invention for production of propylene oxide.

The process of the present invention is illustrated in FIG. 4. The present process provides a recycle which is substantially more efficient and, unexpectedly, capable of effectively utilizing air or oxygen-enriched air as a feed to the oxidation reactor. Specifically, the subject process utilizes a pressure swing adsorption (PSA) unit to effectively remove oxygen, carbon oxides, hydrogen, light hydrocarbons, and nitrogen (if present) from the quench tower effluent. Therefore, the selective oxidation reactor can be comparatively small in terms of capital expenditure and have a long life, yet still effectively remove the minor amount, i.e. up to 2 percent by volume, of oxygen from the recycle feed to the dehydrogenator. The configuration of the subject process eliminates the substantial loss of efficiency inherent in the process of FIG. 2 via the use of the purge stream. Further, steam is not required in the dehydrogenator of the present invention, thereby providing an additional saving of energy.

Referring to FIG. 4, propane is fed into the dehydrogenator where it is converted to propylene. For increased catalyst life, it is preferred to introduce a hydrogen-containing gas into the dehydrogenator with the propane feed. The required amount of hydrogen can conveniently be provided through the recycle stream from the PSA unit as will be discussed below. The hydrogen-containing gas can, if desired, be provided as a discrete stream. The catalyst utilized in the dehydrogenator can be any conventional dehydrogenation catalyst, preferably one or more Group VIII noble metals such as platinum on an alumina support. The dehydrogenator typically operates at a temperature of from about 500° to 800° C., preferably from about 550° to 700° C. The effluent product stream from the dehydrogenator comprising unreacted propane, propylene and hydrogen, is fed into a conventional oxidation reactor along with pure oxygen, air or, preferably, oxygen-enriched air.

The oxidation reactor utilized in the present process is conventional and may employ either a fixed, fluidized or slurry bed reactor design and appropriate catalyst. The reaction may be carried out either in gas or liquid phase. If it is carried out in a liquid phase, a suitable solvent may also be employed The reactor contains a suitable oxidation catalyst such as silver oxide, molybdenum oxide, rhethenium oxide, or lanthanum oxide, alone or in combination with others, and they may be supported or unsupported. Various catalysts are disclosed, for example, in Fenton. U.S. Pat. No. 3,316,279, Waddan et al., European Patent Appln. No. 0 043 192, Bryce Smith. Great Britain Patent No. 1,409,421, Bobolev, Great Britain Patent Nos. 1,433,885, and 1,433,886, Kolombos et al.. U.S. Pat. Nos. 3,888,889. Additional suitable catalysts are known to those skilled in the art.

The oxidation reaction is conducted at a temperature of from about 100° to 500° C., preferably from about 150° to 350° C, at a pressure typically in the range of from about zero (0) to 1000 psig, preferably from about 15 to 750 psig. The reactor residence times vary depending upon the catalyst, as is well know to those skilled in the art, from a few seconds up to 1 hour. The oxygen-containing gas feed may be pure oxygen, air or oxygen-enriched air. In accordance with this invention, oxygen-enriched air preferably contains from about 30 to 80, most preferably from about 55 to 65, percent by volume of oxygen. Such mixtures may be produced by adjusting the capacity of a conventional oxygen-producing unit, e.g. a conventional pressure swing adsorption unit, or by mixing pure oxygen with air in the proper proportions. The ratio of oxygen to propylene in the feed converted to products is suitably in the range of from about 0.8:1 to 2.0:1 by volume.

The effluent from the oxidation reactor comprises a major amount of propylene oxide and minor amounts of acetone, acetaldehyde, formaldehyde, carbon oxides, and nitrogen, when present in the feed, as well as unreacted oxygen, propylene and propane. This gaseous mixture is quenched or scrubbed with a liquid, such as water, to dissolve the water-soluble compounds for subsequent separation and recovery of propylene oxide.

The gas phase effluent from the quench step is introduced into a separator, e.g., a membrane unit, an absorber, a pressure swing adsorption (PSA) unit or a cryogenic system. These separators can be used alone or in combination depending on whether pure oxygen or enriched air is utilized as the feed as is well known to those skilled in the art. For example, if enriched air is used as the feed, a membrane followed or preceded by a PSA unit can be used to prevent any nitrogen accumulation. For purpose of illustration, a PSA unit will be used.

PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudocontinuous flow of desired product. It is preferred to pass the quench tower effluent through a conventional dryer (not shown) to remove moisture therefrom prior to introducing it into the PSA unit.

It may be necessary to raise the pressure of the quench tower effluent in a compressor or other suitable means prior to introducing it into the PSA unit. The compressor increases the pressure of the quench tower gaseous effluent to the operating pressure of a PSA unit, which typically functions from about 3 to 50 psi, preferably from about 20 to 40 psi, higher than the quench tower. These ranges may vary to an extent depending on the adsorbent in the PSA unit.

The adsorbent in the PSA unit may be any art-recognized material which will adsorb propane and propylene to a substantially greater degree than carbon oxides, nitrogen and oxygen, or vice versa. Silica gel or a conventional molecular sieve material, such as 4A zeolite, are preferred adsorbent materials. Silica gel is a particularly preferred material where oxygen-enriched air is utilized as a reactor feed material.

The PSA unit produces a recycle stream and a waste stream. The latter is comprised of oxygen, carbon oxides, e.g. carbon monoxide and carbon dioxide, nitrogen, where the oxidation reactor feed is air or oxygen-enriched air, and $C_{1-2}$ hydrocarbons, e.g. methane, ethane and ethylene, as well as trace amounts of propane and propylene. The PSA recycle stream contains propane, propylene, and a minor quantity of oxygen, typically less than about 2 percent by volume of oxygen.

The oxygen content in the recycle stream would ordinarily have an adverse effect on the efficiency of the dehydrogenator. This is readily apparent, for example, from Khoobiar et al. wherein it is required that the effluent from the quench tower be fed into a selective oxidation reactor.

The use in the PSA unit of an adsorbent, such as a silica gel, which will adsorb propane and propylene will cause substantially all of the hydrogen in the quench tower effluent to be withdrawn and removed in the waste stream. Therefore, it is necessary to add an appropriate quantity of hydrogen to the propane/propylene recycle stream before introducing it into the dehydrogenator. Where an adsorbent which adsorbs carbon dioxide, such as 4A zeolite molecular sieve, is used as the adsorbent in the PSA unit, the hydrogen will be withdrawn in the recycle stream. Therefore, it will not be necessary to add hydrogen thereto In fact, it will typically be necessary to remove some hydrogen therefrom to prevent excessive build-up in the system.

In a preferred embodiment of the present invention, a PSA system comprising parallel PSA units each containing one of the two types of adsorbers mentioned above is utilized wherein the feed is disproportionately divided between them so that the combined effluents contain the desired amount of hydrogen The waste streams are discarded. The amount of hydrogen required in the recycle feed to the dehydrogenator will vary with the catalyst and can be determined by one skilled in the art.

The selective oxidation reactor is of conventional configuration and contains an art-recognized catalyst capable of selectively catalyzing the reaction of oxygen and hydrogen to form water, i.e. the oxidation of hydrogen, without causing oxidation of the desired hydrocarbons, e.g. propane and propylene, in the PSA effluent. Such catalysts and their use are well known in the art. Suitable catalysts include noble metals or base metals, particularly platinum or palladium on alumina.

The oxidation reactor utilized to treat the PSA effluent in the process of the present invention requires only a modest capital expenditure in comparison with the multiple bed unit contemplated in the process illustrated in FIG. 3 since the PSA effluent in the process of the present invention contains about one to two percent by volume of oxygen. Typically, the oxygen content of the PSA effluent in the present process is on the order of from about 0.01 to 2 percent by volume. Since the oxygen content is at such a low level, a small oxidation reactor consisting of a single bed without the need for catalyst regeneration over a period of several years is more than adequate in the process of this invention.

For the production of propylene oxide from propane as illustrated in FIG. 4, total flows in moles and compositions in mole percent based on 100 moles of propylene oxide produced are presented in Table I. The propane feed is substantially 100 percent propane and the fresh feed to the oxidation reactor is substantially pure oxygen. The data expressed in Table I represent operation of the system under conditions such that 20 percent by volume of the propylene in the feed to the oxidation reactor is converted to different products, including propylene oxide, in the oxidation reactor.

In Tables I and II, Point A is the feed into the dehydrogenator after the stream from the oxidation reactor has been combined with fresh propane, Point B is the combined feed into the oxidation reactor, Point C is the oxidation reactor effluent, Point D is the quench tower gaseous effluent to the PSA unit, Point E is the recycle stream from the PSA unit and Point F is the PSA unit waste stream. As previously mentioned, the amount of hydrogen in the feed to the dehydrogenator will vary with the catalyst and reaction conditions used, and may be negligible. For purposes of comparing results given in Tables I and II, hydrogen was not included in the dehydrogenator feed, Point A.

For the examples shown in Tables I and II, silica gel is the adsorbent. Propylene conversion is defined as moles of propylene converted to moles of propylene fed to the oxidation reactor. For example, in Table 1:

$$\text{Conversion} = 100 \times \frac{1597.3 \times .447 - 1553.7 \times .368}{1597.3 \times .447}$$

$$= 19.9\%$$

TABLE I

Propane to Propylene Oxide (PO) Process — Pure $O_2$ Feed
Propylene Conversion = 20%

| Component | A % | B % | C % | D % | E % | F % |
|---|---|---|---|---|---|---|
| $C_3H_6$ | 50.0 | 48.9 | 40.3 | 47.1 | 61.3 | 8.7 |
| $C_3H_8$ | 43.8 | 19.5 | 20.1 | 23.6 | 30.7 | 4.4 |
| $O_2$ | — | 13.6 | 2.0 | 5.9 | 0.4 | 20.6 |
| Propylene Oxide | — | — | 7.1 | — | — | — |
| Acetone | — | — | 0.6 | — | — | — |
| ACOH | — | — | 0.5 | — | — | — |
| HCHO | — | — | 0.3 | — | — | — |
| $CH_3CHO$ | — | — | 0.3 | — | — | — |
| CO | 0.0 | 0.0 | 0.6 | 0.7 | 0.1 | 2.5 |
| $CO_2$ | 4.7 | 3.5 | 8.2 | 5.3 | 5.8 | 3.9 |
| $H_2O$ | — | — | 5.1 | — | — | — |
| $CH_4$ | 0.7 | 2.4 | 2.5 | 3.0 | 0.8 | 8.7 |
| $C_2H_4$ | 0.1 | 0.5 | 0.5 | 0.6 | 0.2 | 1.8 |
| $C_2H_6$ | 0.2 | 0.7 | 0.8 | 0.9 | 0.2 | 2.6 |
| $H_2$ | 0.4 | 10.8 | 11.2 | 13.0 | 0.5 | 46.8 |
| Flow, moles | 1086.4 | 1461.9 | 1418.3 | 1212.6 | 885.1 | 327.4 |

Again utilizing a system as shown in FIG. 4 for the production of propylene oxide from propane, the oxygen feed to the oxidation reactor was changed to an equal mixture of pure oxygen and air which produced oxygen-enriched air containing approximately 60 percent by volume of oxygen. The total flow in moles is shown in Table II. The data expressed in Table II represent operation of the system under conditions such that 20 percent by volume of the propylene in the feed to the oxidation reactor is converted therein to different products, including propylene oxide.

TABLE II

Propane to Propylene Oxide Process — 50% $O_2$ + 50% Air Feed
Propylene Conversion = 20%

| Component | A % | B % | C % | D % | E % | F % |
|---|---|---|---|---|---|---|
| $C_3H_6$ | 50.0 | 44.7 | 36.8 | 42.3 | 61.0 | 6.2 |
| $C_3H_8$ | 43.8 | 17.9 | 18.4 | 21.1 | 30.5 | 3.1 |
| $O_2$ | — | 12.6 | 2.0 | 5.8 | 0.4 | 16.0 |
| Propylene Oxide | — | — | 6.4 | — | — | — |
| Acetone | — | — | 0.6 | — | — | — |
| ACOH | — | — | 0.4 | — | — | — |
| HCHO | — | — | 0.3 | — | — | — |
| $CH_3CHO$ | — | — | 0.3 | — | — | — |
| CO | — | — | 0.6 | 0.6 | 0.1 | 1.8 |
| $CO_2$ | 4.7 | 3.2 | 7.5 | 4.8 | 5.8 | 2.8 |
| $H_2O$ | — | — | 4.7 | — | — | — |
| $CH_4$ | 0.7 | 2.2 | 2.3 | 2.6 | 0.8 | 6.2 |
| $C_2H_4$ | 0.1 | 0.5 | 0.5 | 0.5 | 0.2 | 1.2 |
| $C_2H_6$ | 0.2 | 0.7 | 0.7 | 0.8 | 0.2 | 1.9 |
| $H_2$ | 0.4 | 9.9 | 10.2 | 11.7 | 0.5 | 33.2 |
| $N_2$ | — | 8.3 | 8.5 | 9.8 | 0.5 | 27.8 |
| Flow, moles | 1086.4 | 1597.3 | 1553.7 | 1352.1 | 889.5 | 462.6 |

The process of this invention is advantageous in that it is more efficient and less costly than prior art processes. It is readily apparent from the data present in Tables I and II that unlike the process of the present invention, the process illustrated in FIG. 3 continually removes propane and propylene from the system, thereby sharply reducing the efficiency thereof. Khoobiar et al. states that propane and propylene are removed from the purge stream before it is vented which requires an additional sizable initial capital expenditure, as well as the continuing operating costs of power, for the refrigeration equipment required for the recovery procedure. The present invention does not require this equipment or power.

The process of the present invention has a comparatively small incidence of build up of any of the components of the various gaseous streams formed or separated at any stage thereof. Further, the present invention can be utilized with air or an oxygen-enriched air feed, heretofore not feasible with a closed loop system. Unexpectedly, the subject process operates at particularly enhanced efficiency with an oxygen-enriched air feed.

The invention has been described with reference to preferred embodiments thereof It will be appreciated by those skilled in the art that various modifications may be made from the specific details given without departing from the spirit and scope of the invention.

We claim:

1. A process for the production of alkylene oxides comprising:
   (a) forming an alkene from a gaseous alkane in a catalytic dehydrogenator;
   (b) introducing said alkene stream and an oxygen source selected from the group consisting of pure oxygen, air or a gas enriched in oxygen relative to air into a suitable oxidation reactor for reaction in the presence of an oxidation catalyst at about 100° to 500° C. 0 to 1000 psig, and a residence time from a few seconds up to 1 hour to produce a gaseous effluent containing said oxide;
   (c) quenching said gaseous effluent in a liquid to form a liquid phase containing said oxide and a gas phase;
   (d) recovering said oxide from said liquid phase;
   (e) introducing the gas phase quench effluent under pressure into a pressure swing adsorption unit to thereby form (i) a waste stream and (ii) a gaseous stream comprising said unreacted alkane, alkene, a minor amount of oxygen, and nitrogen when air or oxygen-enriched air is introduced as the oxygen source into the reactor in step (b);
   (f) introducing said gaseous stream into a catalytic selective oxidation reactor to remove substantially all of the remaining oxygen in said stream; and
   (g) recycling said oxygen-depleted effluent to the beginning stage of the dehydrogenator.

2. A process in accordance with claim 1, wherein the oxygen-depleted effluent is combined with fresh alkane feed before recycle to the dehydrogenator.

3. A process in accordance with claim 1, wherein the alkane is propane, the alkene is propylene and the alkylene oxide is propylene oxide.

4. A process in accordance with claim 1, wherein the oxygen source is oxygen-enriched air containing from about 30 to about 80 percent of oxygen by volume.

5. A process in accordance with claim 4, wherein the oxygen-enriched air contains from about 55 to about 65 percent by volume of oxygen.

6. A process in accordance with claim 1, wherein the gas phase in step (e) is introduced into the pressure swing adsorption unit at a pressure of from about 3 to about 50 psig.

7. A process in accordance with claim 1, wherein the oxygen source is oxygen-enriched air, the pressure swing adsorption unit removes substantially all of the hydrogen from the quench effluent, and the oxygen-depleted effluent is combined with a hydrogen-containing stream before recycle to the dehydrogenator.

8. A process in accordance with claim 7, wherein the hydrogen-containing stream is combined with the gaseous stream of step (e) before introduction to the selective oxidation reactor.

9. A process in accordance with claim 1, wherein the pressure swing adsorption unit contains an adsorbent comprising silica gel or a molecular sieve.

10. A process in accordance with claim 1, wherein the oxygen source is pure oxygen.

11. A process in accordance with claim 1, wherein the oxygen source is pure oxygen, the gaseous stream of step (e) contains substantially all of the hydrogen in the quench effluent and said gaseous stream effluent is treated to remove excess hydrogen before recycle to the dehydrogenator.

12. A process in accordance with claim 1, wherein the temperature in the dehydrogenator is from about 500° to about 800° C.

13. A process in accordance with claim 1, wherein the alkane is ethane, the alkene is ethylene, and the oxide is ethylene oxide.

14. A process in accordance with claim 1, wherein the gas phase quench effluent of step (c) is divided, with the resultant divided streams introduced into two pressure swing adsorption units operating in parallel, each unit containing a different adsorbent such that the first gaseous stream formed in the first pressure swing adsorption unit contains a portion of the hydrogen, whereas the second gaseous stream formed in the second pressure swing adsorption unit contains no hydrogen, and wherein the gas phase of step (c) is divided disproportionately between said pressure swing adsorption units so that the gaseous streams formed by said pressure swing adsorption units, when combined, contain a predetermined concentration of hydrogen.

15. A process in accordance with claim 14, wherein the first pressure swing adsorption unit which produces a hydrogen-containing first gaseous stream contains a 4A zeolite molecular sieve adsorbent and the second pressure swing adsorption unit conttains a silica gel adsorbent.

16. A process for the production of alkylene oxides comprising:
   (a) forming an alkene from a gaseous alkane in a catalytic dehydrogenator;
   (b) introducing said alkene stream and an oxygen source selected from the group consisting of pure oxygen, air or a gas enriched in oxygen relative to air into a suitable oxidation reactor for reaction in the presence of an oxidation catalyst at about 100° to 500° C. 0 to 1000 psig, and a residence time from a few seconds up to 1 hour to produce a gaseous effluent containing said oxide;
   (c) quenching said gaseous effluent in a liquid to form a liquid phase containing said oxide and a gas phase;
   (d) recovering said oxide from said liquid phase;
   (e) introducing the gas phase quench effluent under pressure into a separation unit to thereby form (i) a waste stream and (ii) a gaseous stream comprising said unreacted alkane, alkene, a minor amount of oxygen, and nitrogen when air or oxygen-enriched air is introduced as the oxygen source into the reactor in step (b);

(f) introducing said gaseous stream into a catalytic selective oxidation reactor to remove substantially all of the remaining oxygen in said stream; and
(g) recycling said oxygen-depleted effluent to the beginning stage of the dehydrogenator.

17. A process in accordance with claim 16, wherein the separator is chosen from the group consisting of a membrane, an absorber, a pressure swing adsorption unit, a cryogenic system, and combinations thereof.

* * * * *